(12) United States Patent
Wang et al.

(10) Patent No.: US 11,676,735 B2
(45) Date of Patent: Jun. 13, 2023

(54) GENERATION OF MEDICAL RECORDS BASED ON DOCTOR-PATIENT DIALOGUE

(71) Applicant: International Business Machines Corporation, Armonk, NY (US)

(72) Inventors: Ke Wang, Beijing (CN); Jian Min Jiang, Beijing (CN); Jian Wang, Beijing (CN); Jing Li, Beijing (CN); Songfang Huang, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 299 days.

(21) Appl. No.: 16/569,818

(22) Filed: Sep. 13, 2019

(65) Prior Publication Data
US 2021/0082585 A1   Mar. 18, 2021

(51) Int. Cl.
| | | |
|---|---|---|
| *G16H 80/00* | (2018.01) | |
| *G06N 5/022* | (2023.01) | |
| *G06N 20/00* | (2019.01) | |
| *G06N 3/08* | (2023.01) | |
| *G16H 15/00* | (2018.01) | |
| *G16H 10/60* | (2018.01) | |
| *G10L 15/26* | (2006.01) | |

(52) U.S. Cl.
CPC .......... *G16H 80/00* (2018.01); *G06N 5/022* (2013.01); *G06N 20/00* (2019.01); *G10L 15/26* (2013.01); *G16H 10/60* (2018.01); *G06N 3/08* (2013.01); *G16H 15/00* (2018.01)

(58) Field of Classification Search
CPC ........ G16H 80/00; G16H 10/60; G16H 15/00; G16H 50/20; G10L 15/26; G06N 5/022; G06N 20/00; G06N 3/08; G06N 3/0445; G06N 3/0454
See application file for complete search history.

(56) References Cited

U.S. PATENT DOCUMENTS

| | | | |
|---|---|---|---|
| 10,770,180 B1* | 9/2020 | Kemp | G06N 3/0445 |
| 11,062,704 B1* | 7/2021 | Kodish-Wachs | G10L 21/028 |
| 2018/0018966 A1 | 1/2018 | Leonard | |

(Continued)

FOREIGN PATENT DOCUMENTS

| | | | | |
|---|---|---|---|---|
| WO | WO-2018011426 A1 * | 1/2018 | ......... | G06F 16/2465 |
| WO | WO-2018098442 A1 * | 5/2018 | ............. | G10L 15/16 |
| WO | WO-2019022779 A1 * | 1/2019 | ......... | F02M 51/0671 |

OTHER PUBLICATIONS

Kazi et al., Automatically Generating Case Notes From Digital Transcripts of Doctor-patient Conversations Using Text Mining, Jan. 28, 2019, PeerJPreprints, pp. 1-6. (Year: 2019).*

(Continued)

*Primary Examiner* — Christopher L Gilligan
(74) *Attorney, Agent, or Firm* — Patterson + Sheridan, LLP

(57) ABSTRACT

Methods and apparatus for generating medical records from a doctor-patient dialogue are provided. A main content portion of a written doctor-patient conversation is identified. The main content portion of the conversation is extracted from the conversation. The main content of the conversation is divided into sections according to a pre-defined set of sections, and, based on the sections and their respective content, a medical record is generated according to a pre-defined template. The pre-defined template is one of a hard medical record format or a soft medical record format.

20 Claims, 10 Drawing Sheets

(56) References Cited

U.S. PATENT DOCUMENTS

| | | |
|---|---|---|
| 2018/0068074 A1 | 3/2018 | Shen |
| 2019/0122766 A1 | 4/2019 | Strader et al. |
| 2019/0347269 A1* | 11/2019 | Xu .................. G06F 16/258 |
| 2020/0176098 A1* | 6/2020 | Lucas ................ G16H 70/40 |
| 2020/0185102 A1* | 6/2020 | Leventhal ............ G06N 20/00 |
| 2020/0365243 A1* | 11/2020 | Swisher ............... G16H 80/00 |
| 2021/0057068 A1* | 2/2021 | Dandala ............. G06N 3/0454 |
| 2022/0075944 A1* | 3/2022 | Du .................. G06F 40/295 |

OTHER PUBLICATIONS

Authors et. al.: Disclosed Anonymously, "Cognitive reporting of doctor-patient consultation." IP.com No. IPCOM000247997D, IP.com Electronic Publication Date: Oct. 14, 2016, 3 pages.

* cited by examiner

Patient: "Hello doctor! Can you spare me a few minutes?
Doctor: Certainly! Come in and sit down. Now, what is the matter with you?
P: That is just what I want you to tell me.

*D: Well, tell me how you are suffering?*
*P: I seem to be generally out of sorts. I have no appetite for my food, and yet I am always suffering from indigestion.*
*D: Are you troubled with headaches?*
*P: Yes, I am. And what is worse I cannot sleep at night.*
*D: I see. What is your work?*
*P: I am a clerk in an office, and have to work long hours.*
*D: What sort of exercise do you take in the evening?*
*P: I am afraid I don't take any. I feel so tired when I get home that I simply want to sit down, or go to bed.*
*D: I see. Well, you are evidently run down, and need a rest and change. All your troubles are signs of nervous exhaustion. I will give you a nerve tonic but the main thing is rest. If you do as I say, you will soon be all right.*

P: Thank you, doctor. I will follow your advice, Good night!
D: Good night! And let me know how you get on.

FIG. 1

- Patient Information
  - Name, age, gender, occupation
- Chief complaint
  - Symptom
- History of present illness
- Prior History
- Personal history
- Family History
- Diagnosis
- Medical advice
- Medication
  - Drug Hard Medical Record Format 520

- Patient Information
  - Occupation: clerk
- Chief Complaint
  - Symptom: indigestion, headaches, cannot sleep
- History of present illness
- Prior History
- Personal history
- Family History
- Diagnosis
  - Disease: nervous exhaustion
- Medical advice
- Medication
  - Drug: nerve tonic Example Hard Record 510

FIG. 5

Chief Complaint 810

D: Well, tell me how you are suffering?
P: I seem to be generally out of sorts. I have no appetite for my food, and yet I am always suffering from indigestion.
D: Are you troubled with headaches?
P: Yes, I am. And what is worse I cannot sleep at night.

Patient Information 820

D: I see, What is your work?
P: I am a clerk in an office, and have to work long hours.
D: What sort of exercise do you take in the evening?
P: I am afraid I don't take any. I feel so tired when I get home that I simply want to sit down, or go to bed.

Medical Advice 830

D: I see. Well, you are evidently run down, and need a rest and change. All your troubles are signs of nervous exhaustion. I will give you a nerve tonic but the main thing is rest. If you do as I say, you will soon be all right.

Chief Complaint
Patient Information
Medical Advice

Section Types
451

FIG. 8

GENERATION OF MEDICAL RECORDS BASED ON DOCTOR-PATIENT DIALOGUE

BACKGROUND

The present invention relates to deep learning, and more specifically to generation of medical records based on doctor-patient dialogue.

Electronic medical records are desired to facilitate patient care. Health care professionals interacting with patients need to make notes, either by hand or via a computing device, such as a laptop or handheld, for accurate record keeping. However, there is often no fixed format, and the content of the patient's complaint or description of his or her condition, his or her interaction with the health care provider, and any conclusions or advice rendered by that health care provider, that is written into the note or chart is subjective, dependent upon what the care provider then feels is important. While it is possible, in the interests of preserving as much data as possible, to record the dialogue between patient and physician and store the recording together with the chart notes, to actually use the content of the recording someone has to listen to the entirety of it, and rewrite the clinical notes into a more formal record.

Additionally, conventionally, when a subsequent health care provider wishes to learn about the patient's case, they need to access a copy of the chart notes. Because the chart notes are not uniform from case to case, or from visit to visit by the same patient, and, as noted, the content of the chart notes is a function of the subjectivity of the, for example, physician, nurse, or other clinician (often young resident) writing the chart notes, it is difficult to perform statistical analyses, data mining, or other data processing and analysis functions on large numbers of chart notes, as they are not readily mutually compared.

It is useful to provide solutions to these problems of health care charts.

SUMMARY

According to one embodiment of the present disclosure, a method is provided. The method includes identifying a main content portion of a written record of a doctor-patient conversation, extracting the main content portion from the conversation, and dividing the main content portion into sections according to a pre-defined set of sections. The method further includes, based on respective contents of the sections, generating a medical record according to a pre-defined template.

According to a second embodiment of the present disclosure, a computer-readable storage medium is provided. The computer-readable storage medium has computer-readable program code embodied therewith, the computer-readable program code executable by one or more computer processors to perform an operation. The operation includes identifying a main content portion of a written record of a doctor-patient conversation, extracting the main content portion from the conversation, and dividing the main content portion into sections according to a pre-defined set of sections. The operation further includes, based on respective contents of the sections, generating a medical record according to a pre-defined template.

According to a third embodiment of the present disclosure, a system is provided. The system includes a main content extractor, configured to extract a main portion of a written doctor-patient conversation, a section extractor, configured to assign individual statements of the main portion to corresponding sections of the main portion, and a medical record generation engine, configured to, based on respective contents of the sections, generating a medical record according to a pre-defined template.

BRIEF DESCRIPTION OF THE SEVERAL VIEWS OF THE DRAWINGS

FIG. 1 illustrates an example dialogue between a doctor and patient, according to one embodiment disclosed herein.

FIG. 5 illustrates an example hard medical record generated from the dialogue of FIG. 1 and a corresponding hard medical record format, according to one embodiment disclosed herein.

FIG. 8 illustrates the example dialogue of FIG. 1 as divided into three sections, according to the soft record format of the example system of FIG. 6, according to an embodiment disclosed herein.

DETAILED DESCRIPTION

Figure 2:
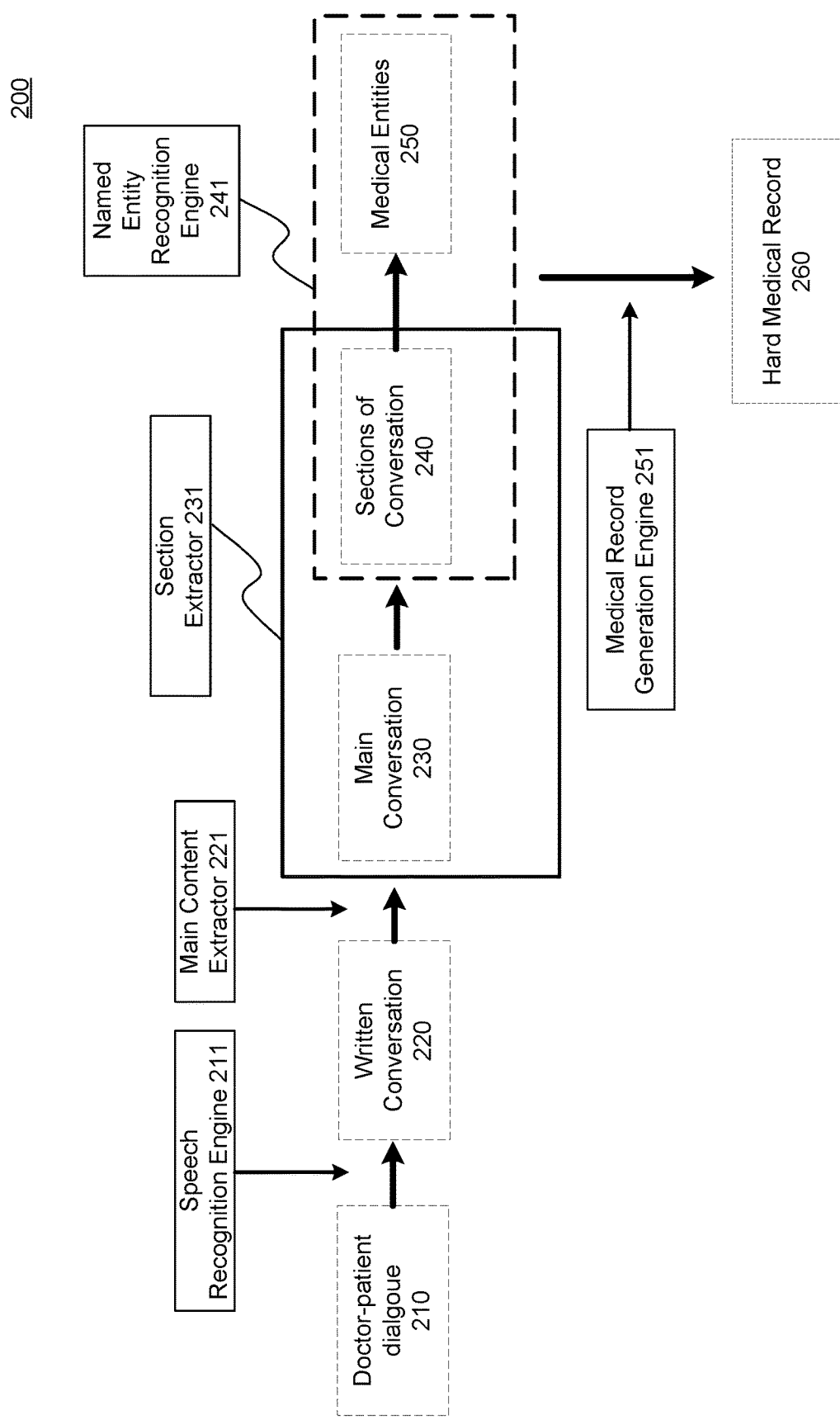
FIG. 2 illustrates an example system for generating medical records according to a hard record format, according to one embodiment disclosed herein.

In embodiments, a deep learning method is used to generate medical records from doctor-patient dialogue. The medical records that are generated may be based upon either a hard medical template or a soft medical template. In embodiments, an input to an example method is a written record of a conversation between a doctor and a patient. In some embodiments, the written record is generated by applying speech recognition to an audio recording of the doctor-patient dialogue. In embodiments, the method outputs medical records according to a pre-defined template.

With reference now to FIG. 1, an example dialogue 100 between a doctor and his or her patient is illustrated, in accordance with various embodiments. With reference thereto, the example dialogue is divided into three portions. Portion 110 is an opening section at the beginning of the doctor-patient interaction, where pleasantries may be exchanged, but no key words or terms are supplied by either the doctor or the patient that may be of use for the purposes of automated medical record generation. Portion 120 is the relevant portion of the dialogue, and as described more fully below with reference to FIG. 4, portion 120 includes the source material that is used to generate the medical record. For this reason, portion 120 may be sometimes referred to herein as the "main portion." Finally, portion 130 is a closing section, which may contain greetings or the like, but is also irrelevant as concerns data to be used or included in a medical record.

Continuing with reference to FIG. 1, portion 120 thus includes several question and answer (QA) pairs, and ends with a summation statement 121 made by the doctor, which includes both his diagnosis as well as his recommended treatment plan.

It is noted that a medical record generated according to embodiments disclosed herein may have a variety of formats. For example, it may be generated according to a hard medical record format, or, alternatively, according to a soft medical record format. In embodiments, the hard format may have some additional details relative to the soft format, for example. Example systems used to generate each format may be slightly different, as described below with reference to FIGS. 2 and 6, respectively. Next described is FIG. 2, which illustrates an example system 200 for generating medical records according to a hard record format, according to one embodiment disclosed herein.

With reference to FIG. 2, there are shown both elements of the example system 200, which are provided in boxes with solid outlines, as well as the original input 210 to system 200, all intermediate results (220 through 250), and the ultimate output of the system, hard medical record 260, all shown in blocks with dashed outlines. In addition, index numbers of the system elements end in a "1", and index numbers of the input, output and intermediate results end in a "0".

Continuing with reference to FIG. 2, beginning at the far left of the figure, there is shown an example doctor-patient dialogue 210, which is the input to the system. As noted above, doctor-patient dialogue 210 may be an audio recording, such as, for example, an audio file, received from a doctor, who recorded an interaction with a patient, and who wants a medical record for the patient's visit to be generated. As shown in FIG. 2, doctor-patient dialogue 210 is input to speech recognition engine 211, which transforms the audio file into a written conversation. In embodiments, this is a necessary transformation, inasmuch as the deep learning tools used to generate a medical record operate on written text, including words, QA pairs, identified medical entities, and other statements, and not on sound elements, or units of speech, of an audio recording. Thus, in embodiments, a written input is needed to facilitate that deep learning processing. In some embodiments, at the speech recognition level, the individual voices of the two speakers may be identified, in addition to the words and sentences they utter, which increases the accuracy of who is the speaker in each QA pair of the dialogue. Thus, in such embodiments, the sentences uttered by "D" and "P", as shown in FIG. 1, are identified at the speech recognition level. In alternate embodiments, the author of each sentence may be performed after the written conversation has been generated from the audio.

Continuing with reference to FIG. 2, the output of speech recognition engine 211 is written conversation 220. This is input to main content extractor 221, which extracts a main, or relevant portion of the written conversation 220. For example, for the doctor-patient dialogue 100 shown in FIG. 1, the extracted portion is main portion 120.

Figure 4:
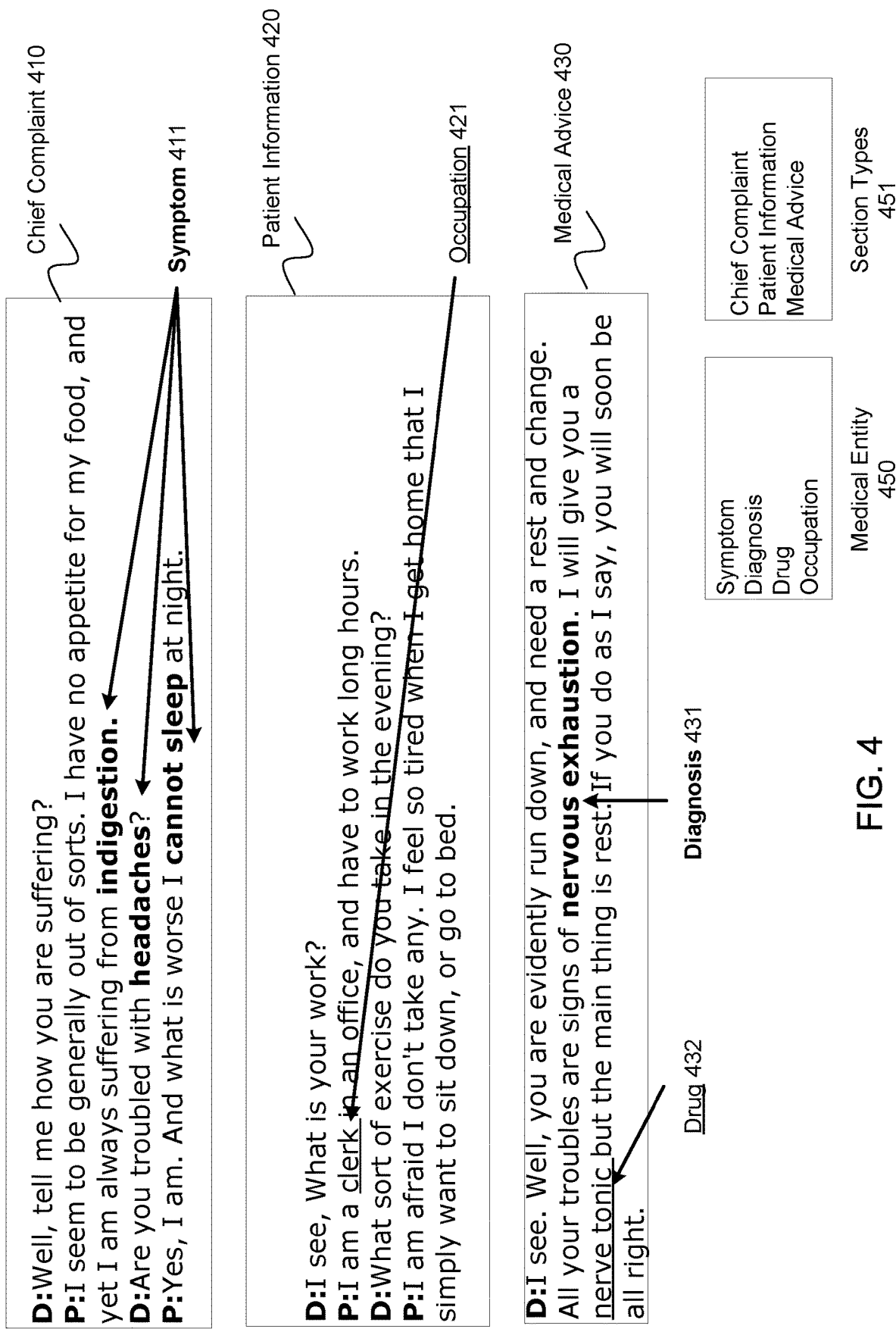
FIG. 4 illustrates the example dialogue of FIG. 1 after being divided into three sections, with named medical entities identified in each section, according to one embodiment disclosed herein.

Continuing further with reference to FIG. 2, the output of main content extractor 221 is main conversation 230. Main conversation 230 is input to, and processed by, section extractor 231 to yield several sections, shown in FIG. 2 as sections of conversation 240. In embodiments, QAs and other statements of main conversation 230 are assigned to respective elements of a set of pre-defined sections of a medical record format. In the example system of FIG. 2, this is a hard medical record format. In some embodiments the pre-defined sections include a chief complaint section, a patient information section, and a medical advice section. An example of how the main portion 120 of the doctor-patient dialogue of FIG. 1 is processed into three sections of an example hard medical record format is illustrated in FIG. 4, described below.

Continuing further with reference to FIG. 2, the output of section extractor 231, sections of conversation 240, is the input to named entity recognition engine 241, and thus, for illustrative purposes, section extractor 231 is shown as overlapping with, or intersecting, named entity recognition engine 241, precisely at sections of conversation 240. Named entity recognition engine 241 is configured to recognize various types of words or phrases of relevance to generating a medical record according to the hard medical record format, such as, for example, a symptom, a diagnosis, a drug, or an occupation, as shown in FIG. 4 at block 450, for example. The output of named entity recognition engine 241 is medical entities 250.

Continuing still further with reference to FIG. 2, both sections of conversation 240, and medical entities 250, are input to medical record generation engine 251. From these inputs, medical record generation engine 251 generates a hard medical record 260, the ultimate output of system 200. An example hard medical record in accordance with various embodiments, generated from the main portion 120 of doctor-patient dialogue 100 of FIG. 1, is presented in FIG. 5, at 510.

Figure 3:
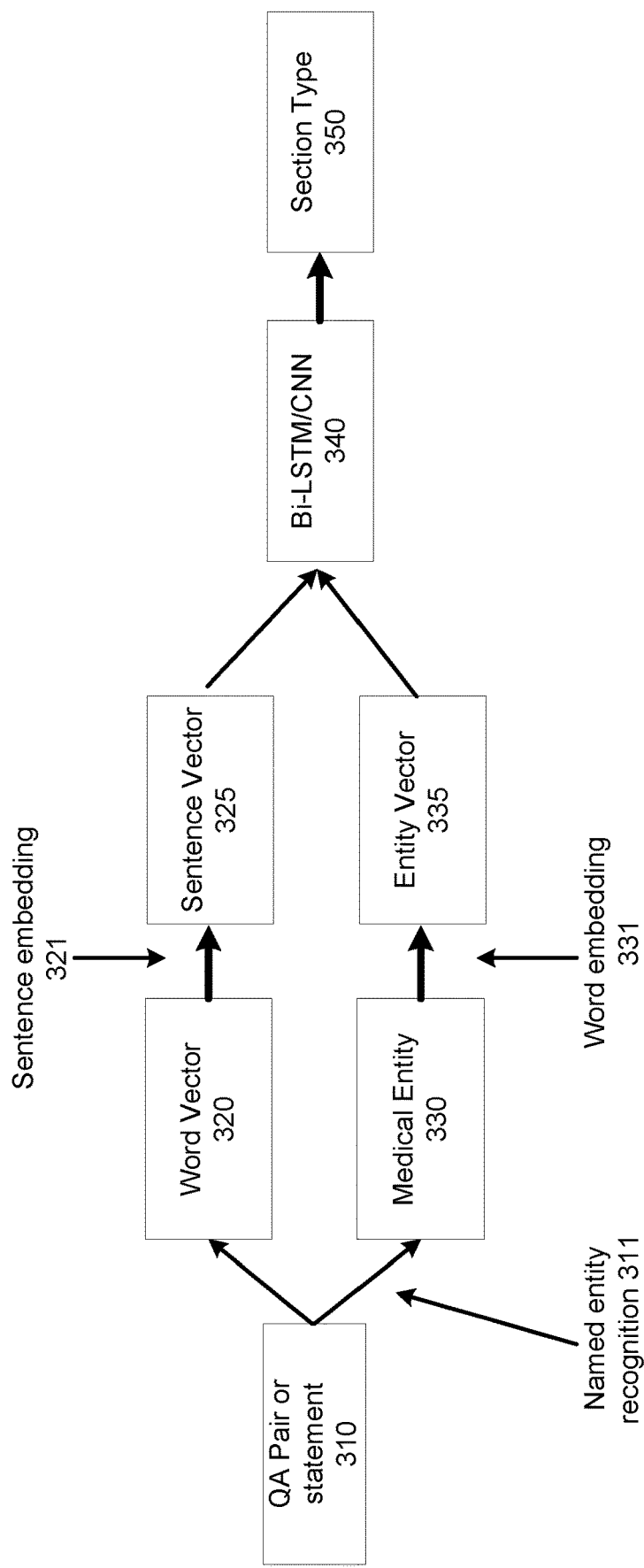
FIG. 3 illustrates assignment of a question and answer pair from an example doctor-patient dialogue to a section type, according to one embodiment disclosed herein.

FIG. 3 illustrates an example process 300 for assignment of a QA pair, or a statement which is not part of a QA pair, the QA pair or (isolated) statement taken from an example doctor-patient dialogue, to a section type according to one embodiment disclosed herein. In embodiments, this process may be performed by section extractor 231 of system 200 of FIG. 2, described above. In embodiments, section extractor 231 would perform this process for each QA pair and for each isolated statement of the main portion of a doctor-patient conversation.

With reference to FIG. 3, beginning with QA pair or statement 310, the QA pair or statement 310 is processed to generate one or more word vectors 320 and one or more identified medical entities 330. The identified medical entities 330 are so identified using named entity recognition 311. For example, the second QA pair of main portion 120 of the doctor-patient dialogue 100 of FIG. 1 reads as follows:

D: Are you troubled with headaches?

P: Yes, I am. And what is worse I cannot sleep at night.

As an example, process 300, operating on this QA pair, associates each of the words "troubled" "worse" and "night" with a word vector 320, and recognizes each of the terms "headaches" and "cannot sleep" as a medical entity 330.

As another example, the last sentence of main portion 120 of the doctor-patient dialogue 100 of FIG. 1 reads as follows:

D: Well, you are evidently run down, and need a rest and change. All your troubles are signs of nervous exhaustion. I will give you a nerve tonic but the main thing is rest. If you do as I say, you will soon be all right.

This is not a QA pair that begins with a question initiated by the doctor, but rather an isolated summation sentence of the doctor. Process 300, for example, associates each of the words "run down", "rest", "change" and "troubles" with a word vector 320, and recognizes each of the terms "nervous exhaustion" and "nerve tonic" as a medical entity 330.

Continuing with reference to FIG. 3, each generated word vector is processed using sentence embedding 321 to yield a sentence vector 325, and, in parallel, each identified medical entity 330 is processed using word embedding 331 to yield an entity vector 335. As shown, each sentence vector 325 and each entity vector 335 is input to a Bidirectional Long Short-Term Memory (BI-LSTM)/convolutional neural network (CNN) model, which identifies which section type 350, of a set of pre-defined section types used to categorize the doctor-patient dialogue, the QA pair or isolated statement 310, as the case may be, is to be assigned to. Bi-LSTM/CNN model 340 is a deep learning model to learn abstract features with context from input features. In embodiments, the pre-defined section types may be, as described more fully below with reference to FIG. 4, "chief complaint", "patient information" and "medical advice." Process 300 ends at block 350, with the assignment of the input QA or statement to a section type.

It is noted with reference to FIGS. 2 and 3 that medical entity 330 of FIG. 3 is the same as named entities 250, generated by named entity recognition engine 241, both of FIG. 2. Thus, in the process 300 of FIG. 3, medical entities 330, generated as shown in FIG. 2, may be used to assign a QA pair or, for example, an isolated sentence, to a section type 350. Based on the section type 350, different medical entities are placed into the correct fields of a hard medical record template. It is noted that for the hard format medical record, a key task is filling the hard record template with medical entities. FIG. 4 illustrates the example main portion 120 of example dialogue 100 of FIG. 1 after being divided into three sections, with named medical entities identified in each section, according to one embodiment disclosed herein. The divided example dialogue of FIG. 4 is the result of processing each of the 4 QA pairs of main portion 120, and the isolated doctor's final summation statement of main portion 120, using elements 210 through 250 of system 200 of FIG. 2, which includes the use of process 300 of FIG. 3 by section extractor 231.

With reference to FIG. 4 there is shown a first section, chief complaint 410. Chief complaint section 410 includes the first two QA pairs of the main portion of the dialogue, which deal with the patient describing his problem in response to the doctor's questions. These questions begin with a general query ("how are you suffering?") and become more specific ("are you troubled with headaches?"). In addition, there are three medical entities identified in chief complaint 410. As shown in block 450 at the bottom of FIG. 4, the medical entities relevant to this embodiment are, symptom, diagnosis, drug and occupation. In chief complaint section 410 it is expected that entities relating to the patient's symptoms would be identified. This is the case, and the symptoms "indigestion", "headaches" and "cannot sleep" are in fact identified. These symptoms 411 are shown in bold in the chief complaint 410 section of FIG. 4.

Continuing with reference to FIG. 4, there is also shown a second section, patient information 420. Patient information 420 includes the next two QA pairs of the main portion 120 of the dialogue 100, which deal with the doctor questioning the patient as to his occupation, and the exercise regimen he may follow. Here as well a medical entity term is identified, but this time it is from the "occupation" 421 category of medical entity 450, and it is the word "clerk", shown in underline in in the patient information 420 section of FIG. 4.

Continuing further with reference to FIG. 4, there is also shown a third section, medical advice 430. As shown at the bottom of FIG. 4, in block 451, this is the third and final section type of the pre-defined sections according to the example embodiment of FIG. 4. Medical advice 430 has no QA pair at all. Rather, it has the doctor's summary statement that ends the main portion 120 of the doctor-patient dialogue. This is to be expected, inasmuch as the final section is medical advice, so the doctor generally speaks in this section. Once again, in this medical advice 430 section as well, two words form each of the medical entity 450 categories are identified, namely the diagnosis 431 medical entity "nervous exhaustion", shown in bold in section 430, and finally, the drug 432 medical entity "nerve tonic", shown underlined in section 430.

Given the division into the three pre-defined sections of this example embodiment, and the words that fit into each of the four medical entity categories, as shown in FIG. 4, a medical record may be generated, according to one embodiment disclosed herein. This is next described with reference to FIG. 5.

FIG. 5 illustrates an example hard medical record generated from the processed sections of FIG. 4. FIG. 5 also illustrates a corresponding hard medical record format, according to one embodiment disclosed herein. With reference to FIG. 5, an example record 510 is shown. It follows the example hard record format 520 also shown in FIG. 5. Example record 510 is not fully filled out, as it is illustrative of how the information included in the example main portion 120 of the example dialogue may be identified and used to generate the record. It thus includes the information that the patient provided in the short encounter. As may be seen with reference to example record 510, the five example fields of the record that are filled out are precisely those for which a medical entity was identified, and one that repeats the doctor's advice section 430, as shown in FIG. 4. In detail, the "Patient Information" field of example record 510 has the "occupation" medical entity "clerk." Continuing with the fields of example medical record 510, the "Chief Complaint" field of example record 510 has the three "symptom" medical entity words that were identified, namely "indigestion", "headaches" and "cannot sleep", the "Diagnosis" field of example record 510 has the identified "diagnosis" medical entity phrase "nervous exhaustion", and finally, the "Medication" field of example record 510 has the identified "drug" medical entity phrase "nerve tonic."

In addition to the fields of example record 510 that are tied to the four medical entity categories, the "Medical Advice" field of example record 510 repeats essentially the entire medical advice section 430 of the processed main portion 120 shown in FIG. 4.

Figure 6:
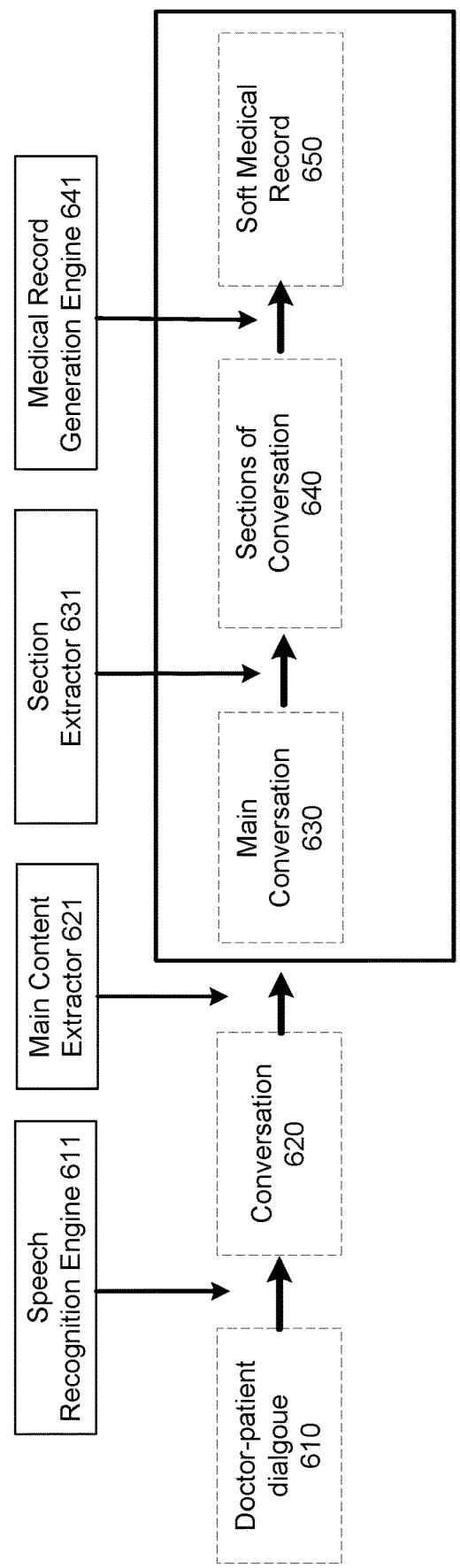
FIG. 6 illustrates an example system for generating medical records according to a soft record format, according to one embodiment disclosed herein.
Figure 7:
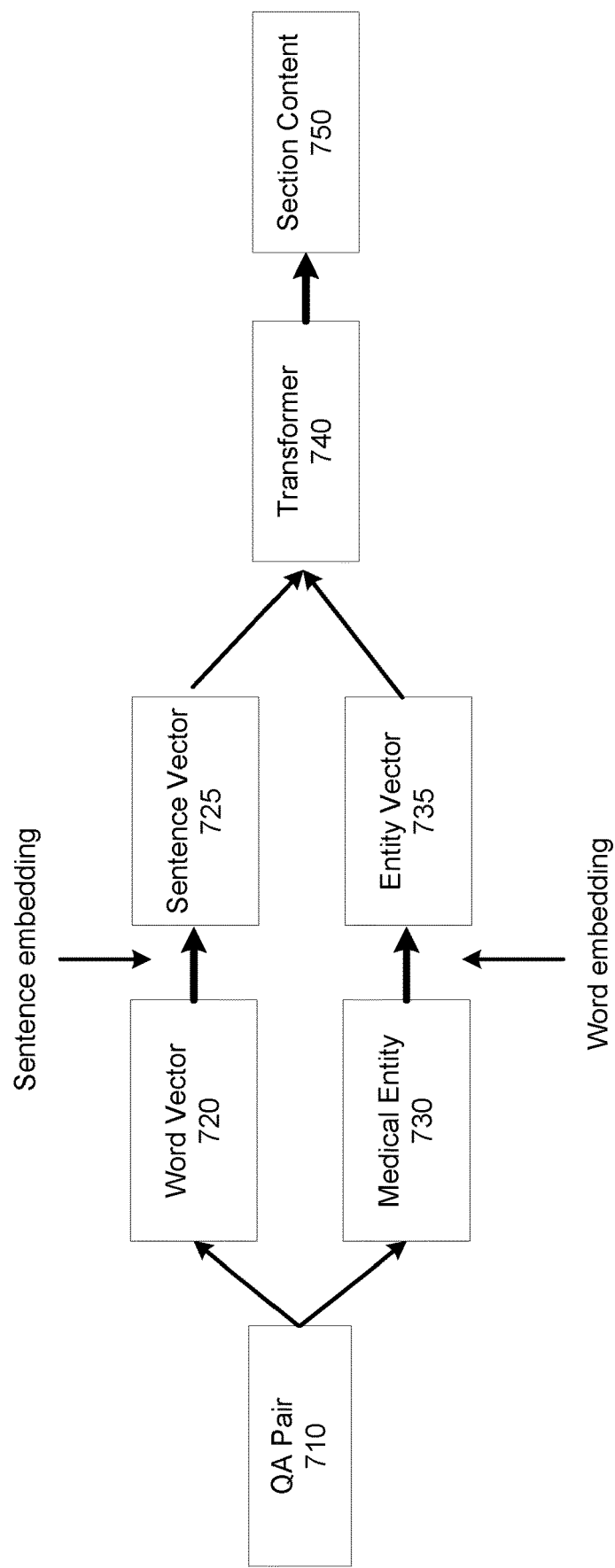
FIG. 7 illustrates details of an example process for assignment of a question and answer pair to a section based on a generative model, according to an alternate embodiment to that illustrated in FIG. 3, disclosed herein.

FIG. 6 illustrates an example system for generating medical records according to a soft record format, according to one embodiment disclosed herein. FIG. 7 illustrates a related process, and FIGS. 7 and 8 illustrate a related example dialogue and example medical record. FIGS. 6 through 9 thus illustrate an alternate embodiment for medical record generation, similar to the embodiment shown in FIGS. 2 through 5, but with some slight changes. As noted, the embodiment of FIGS. 6 through 9 involves generation of a medical record using the soft medical record format, and it is this change that drives the variations in the system of FIG. 6, the section assignment process of FIG. 7, the processed main portion of dialogue shown in FIG. 8, and finally, the example record shown in FIG. 9. These are all next described, but only changes with respect to their counterpart FIGS. 2-5 are described, all else being identical to the respective counterpart figures.

FIG. 6 illustrates an example system 600 for generating medical records according to a soft record format, according to one embodiment disclosed herein. System 600 is identical to system 200 of FIG. 2, except for the absence in system 600 of any counterpart to named entity recognition engine 241 or to medical entity 250 intermediate result, both as shown in FIG. 2. Otherwise the system 600 is identical to system 200 of FIG. 2, described above. The change between the two systems is the result of system 600 not engaging in any named entity recognition (NER) when processing the main portion of an example doctor-patient dialogue. Accordingly, soft medical records 650, which is the ultimate output of system 600 of FIG. 6, is generated directly from the intermediate result sections of conversation 640, without performing any NER.

FIG. 7 illustrates details of an example process 700 for assignment of a question and answer pair to a section based on a generative model, according to an alternate embodiment to that illustrated in FIG. 3, disclosed herein. Process 700 is identical to its counterpart process 300 of FIG. 3, with one exception. At block 740, process 700 does not use a Bi-LSTM/CNN model to assign a section type to the input QA pair 710, as was the case for process 300 of FIG. 3. Rather, process 700, using a generative model, employs a transformer. A transformer is sequence-to-sequence model that is a neural network which transforms a given sequence of elements, such as, for example, the sequence of words in a sentence, into another sequence. Accordingly, in embodiments, transformers may be used to generate medical records. Except for this variation, process 700 is otherwise identical to process 300, described above.

FIG. 8 illustrates the main portion 120 of the example dialogue of FIG. 1 as divided into three sections, according to the soft record format of the example system of FIG. 6, according to an embodiment disclosed herein. FIG. 8's division of the relevant portion of the dialogue is identical to that of FIG. 4, and it assigns the same QA pairs, to the same sections, as does the processed dialogue of FIG. 4, with only one difference. The processed dialogue of FIG. 8 does not have any identification of medical entity categories, or specific words in the dialogue that fit into the medical entity categories, as described above with reference to FIGS. 2-4. This is due to the fact that the generation of the soft medical record format 920 of FIG. 9 does not use NER or its results. Besides this one difference, the processed dialogue of FIG. 8 is otherwise identical to the processed dialogue of FIG. 4, described above. As shown, the three sections of FIG. 8 include a chief complaint 810 section, which includes two QAs, a patient information section 820, which also includes two QAs, and finally a medical advice 830 section, which includes one summation sentence uttered by the doctor. These three sections track the three pre-defined section types 451, as described above.

Figure 9:
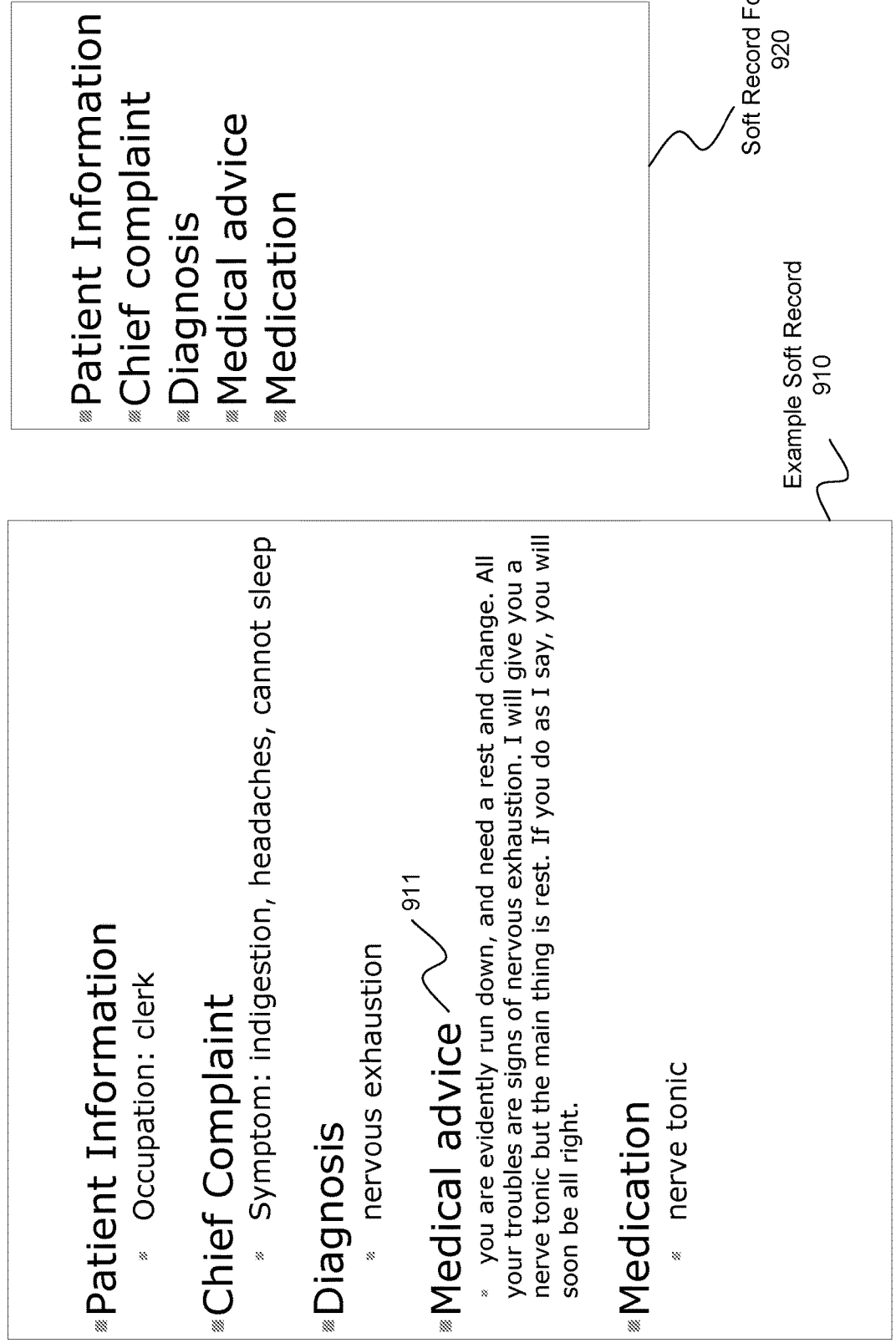
FIG. 9 illustrates an example soft medical record and a corresponding soft medical record format, according to one embodiment disclosed herein.

FIG. 9 illustrates an example soft medical record 910 and a corresponding soft medical record format 920, according to one embodiment disclosed herein. By comparison with FIG. 5, which illustrates an example of hard medical records format, it is seen that the soft medical record format has only five fields, namely "patient information", "chief complaint", "diagnosis" "medical advice" and "medication." As seen in the example soft medical record 910, the medical advice field essentially copies the summation sentence of section 830 of FIG. 8. As noted above, in the soft medical record format, medical records are generated by a transformer model. Thus, between the two methods, the medical record generation engine (block 251 of FIG. 2, and block 641 of FIG. 6, respectively) is different. In the hard medical record format, the medical record generation engine includes a medical template and a section type classifier. In contrast, in the soft format method, the medical record generation engine includes a transformer.

Figure 10:
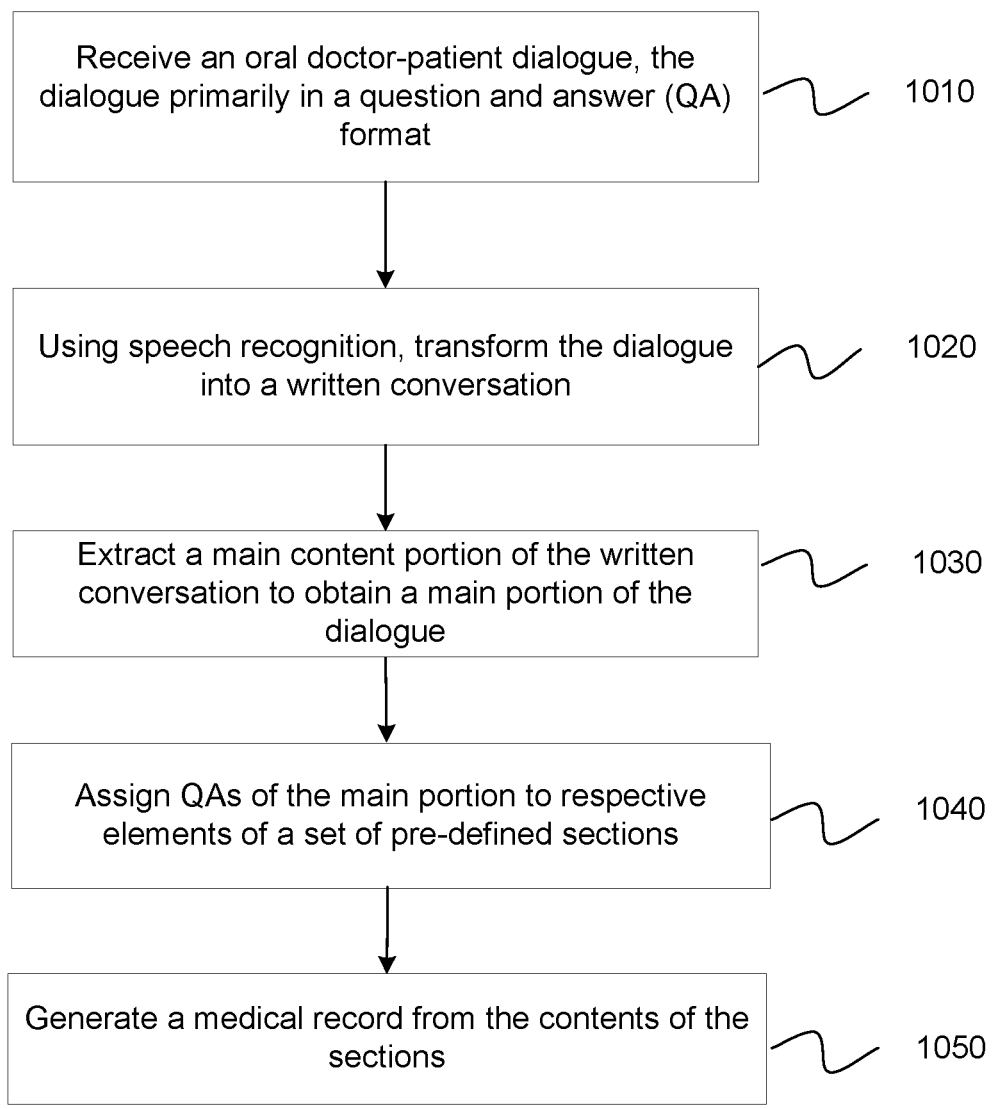
FIG. 10 is a flow diagram illustrating a method to generate medical records from an oral doctor-patient dialogue, according to one embodiment disclosed herein.

FIG. 10 is a flow diagram illustrating a method 1000 to generate medical records from an oral doctor-patient dialogue, according to one embodiment disclosed herein. Method 1000 includes blocks 1010 through 1050. In alternate embodiments, method 1000 may have more, or fewer, blocks. In one embodiment, method 1000 may be performed, for example, by system 200 of FIG. 2, or, for example, by system 600 of FIG. 6.

Continuing with reference to FIG. 10, method 1000 begins at block 1010, where an oral doctor-patient dialogue is received. In some embodiments, the dialogue is primarily in a QA format. For example, the doctor may have had the interview in his office, may have recorded it, and, for example, may then have saved it to his office's computers. For example, from a folder on his computer in which it was saved, the doctor may then have loaded it into a medical record generation program also running on his desktop computer. Or, for example, he may have uploaded it to the cloud, availing himself of, for example, a cloud based application used by his office or group, or alternatively to be processed by a third party medical records generation service.

From block 1010 method 1000 proceeds to block 1020, where, using speech recognition techniques, the oral dialogue is transformed into a written conversation. In embodiments, this is a necessary transformation inasmuch the deep learning tools used to generate a medical record operate on written text, including words and QA pairs, and not intervals or units of speech from an audio recording. Thus, a written input is needed to facilitate that deep learning processing. In some embodiments, at the speech recognition level, the individual voices of the two speakers may be identified, in addition to the words they utter, which increases the accuracy of who is the speaker in each QA pair.

From block 1020, method 1000 proceeds to block 1030, where a main content portion of the dialogue is extracted. Such an example extraction result is shown in FIG. 1, described above, where main portion 120 is extracted for further processing, inasmuch as it includes all of the relevant information needed to generate a medical record.

From block 1030, method 1000 proceeds to block 1040, where QAs of the now extracted main portion are assigned to respective elements of a set of pre-defined sections of a medical record format. In some embodiments, the pre-defined sections include a chief complaint section, a patient information section, and a medical advice section. For example, as shown in FIG. 4, for each of the chief complaint section 410, and the patient information section 420, there are two QA pairs assigned to each. In each QA pair, the doctor ("D") asks questions and the patient ("P") answers. However, in the third section, which is the medical advice section 430, as expected, there may be only one speaker, the doctor, and thus he does not ask any question, but rather gives a medical opinion, including a diagnosis ("nervous exhaustion"), and a treatment plan ("nerve tonic" and "rest").

From block 1040, method 1000 proceeds to block 1050, where a medical record is generated from the contents of the sections. In embodiments, the medical record may be of various formats, such as, for example, a hard medical record format, as shown at 520 of in FIG. 5, or, for example, a soft medical record format, as shown at 920 of FIG. 9. In such embodiments, a similar, but slightly varied process may be used to generate each type of medical record. Thus, for example, in order to generate a hard medical record format type record, the example process 300 of FIG. 3 may be used, which uses a Bidirectional Long Short-Term Memory (BI-LSTM)/convolutional neural network (CNN) approach, which, for example, may be performed using Bi-LSTM/CNN 340 of FIG. 3. Alternatively, for example, in order to generate a soft medical record format type record, the example process 700 of FIG. 7 may be used, which uses a generative model, implemented with a transformer, such as transformer 740 of FIG. 7. With the generation of the medical record, of either type, method 1000 terminates at block 1050.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications that generate medical records from either an audio recording of a doctor-patient dialogue or a written record of such a doctor-patient dialogue or related data available in the cloud. Each health care professional interacting with a given patient could, for example, record all patient interactions, or, for example, first visit interactions for a new condition or sickness, and upload the recordings to the cloud. Or, for example, the recordings may be automatically uploaded periodically by a cloud service. For example, the medical record generation application could execute on a computing system in the cloud and store all medical records that have been generated by it at a storage location in the cloud. The medical record generation application could produce the medical records in a pre-defined format, such as hard or soft format, as described above, or, for example, it could produce them in both formats, and they may be accessed by different users according to the user's preferred format. For example, different insurance companies may desire different formats of medical records to be used in their underwriting, auditing, or claim payment functions. Doing so allows a user to access this information from any computing system attached to a network connected to the cloud (e.g., the Internet), and thus facilitates a central depository of all of a patient's medical records.

While the foregoing is directed to embodiments of the present invention, other and further embodiments of the invention may be devised without departing from the basic scope thereof, and the scope thereof is determined by the claims that follow.

What is claimed is:

1. A method comprising:

identifying a main content portion of a written record of a doctor-patient conversation;

extracting the main content portion from the doctor-patient conversation;

dividing the main content portion into sections according to a pre-defined set of sections;

identifying a section type, of a pre-defined set of section types, to assign at least a first section of the main content portion to, comprising:

generating at least one word vector based on the first section of the main content portion;

generating at least one sentence vector based at least in part on the at least one word vector and a sentence embedding;

generating an entity vector based on at least one medical entity identified in the first section of the main content portion and a word embedding; and assigning the section type to the first section of the main content portion by processing the at least one sentence vector and the entity vector using a trained neural network, wherein:

the trained neural network comprises a bidirectional long short-term (Bi-LSTM) model; and the trained neural network is trained to categorize the generated sentence vector and the generated entity vector into a corresponding section type, of the plurality of pre-defined section types; and based on respective contents of the sections, generating a medical record according to a pre-defined template, wherein:

the pre-defined template comprises a plurality of fields, each respective field of the plurality of fields comprises a respective name that matches a respective section type of the pre-defined set of sections, a first field of the plurality of fields matches the section type assigned to the first section of the main content portion, and the first field is filled with one or more values of the at least one medical entity identified in the first section.

2. The method of claim 1, further comprising:
receiving the doctor-patient conversation in oral form, and using speech recognition, transforming the oral conversation into a written conversation.

3. The method of claim 1, wherein the pre-defined set of sections of the main portion includes a chief complaint section, a patient information section, and a medical advice section.

4. The method of claim 1, wherein the pre-defined template is one of a hard medical record format or a soft medical record format.

5. The method of claim 4, wherein the pre-defined template is a hard medical record format, and further comprising identifying values for one or more pre-defined medical entities in one or more of the sections.

6. The method of claim 5, wherein the medical record includes values for at least one of the pre-defined medical entities.

7. The method of claim 6, wherein the pre-defined medical entities include symptom, diagnosis, drug and patient occupation.

8. The method of claim 1, wherein the doctor-patient conversation includes a plurality of question and answer (QA) pairs.

9. The method of claim 8, wherein dividing the main content portion into sections further comprises assigning each QA pair or other statement to one of the pre-defined set of sections.

10. The method of claim 9, wherein assigning each QA pair or portion of a QA pair to one of the pre-defined sections further comprises:
parsing each QA pair to obtain sentence vectors and entity vectors, and
processing the sentence vectors and entity vectors to identify their section type.

11. A system, comprising:
a processor; and
a memory storage device, including processor-executable instructions that when performed by the processor perform an operation comprising:
identifying a main portion of a written doctor-patient conversation;
extracting the main portion of the written doctor-patient conversation;
identifying a section type, of a pre-defined set of section types, to assign at least a first section of the main content portion to, comprising:
generating at least one word vector based on the first section of the main content portion;
generating at least one sentence vector based at least in part on the at least one word vector and a sentence embedding;
generating an entity vector based on at least one medical entity identified in the first section of the main content portion and a word embedding; and
assigning the section type to the first section of the main content portion by processing the at least one sentence vector and the entity vector using a trained neural network, wherein:
the trained neural network comprises a bidirectional long short-term (Bi-LSTM) model; and
the trained neural network is trained to categorize the generated sentence vector and the generated entity vector into a corresponding section type, of the plurality of pre-defined section types; and
based on respective contents of the sections, generating a medical record according to a pre-defined template, wherein:
the pre-defined template comprises a plurality of fields,
each respective field of the plurality of fields comprises a respective name that matches a respective section type of the pre-defined set of sections,
a first field of the plurality of fields matches the section type assigned to the first section of the main content portion, and
the first field is filled with one or more values of the at least one medical entity identified in the first section.

12. The system of claim 11, wherein the operation further comprises:
receiving a recording of a doctor-patient conversation, and transforming it into a written conversation between the doctor and the patient.

13. The system of claim 11, wherein the pre-defined template is one of a hard medical record format or a soft medical record format.

14. The system of claim 13, wherein the pre-defined template is a hard medical record format, and further comprising a named entity recognition engine configured to identify values for one or more pre-defined medical entities in one or more of the sections.

15. The system of claim 11, wherein the doctor-patient conversation includes a plurality of QA pairs, and wherein the operation further comprises assigning each QA pair or other statement to one of a pre-defined set of sections.

16. A computer program product for generating medical records from a doctor-patient dialogue, the computer program product comprising:
a computer-readable storage medium having computer-readable program code embodied therewith, the computer-readable program code executable by one or more computer processors to:
identify a main content portion of a written record of a doctor-patient conversation;
extract the main content portion from the doctor-patient conversation;
divide the main content portion into sections according to a pre-defined set of sections;
identify a section type, of a pre-defined set of section types, to assign at least a first section of the main content portion to, comprising:
generate at least one word vector based on the first section of the main content portion;
generate at least one sentence vector based at least in part on the at least one word vector and a sentence embedding;
generate an entity vector based on at least one medical entity identified in the first section of the main content portion and a word embedding; and
assign the section type to the first section of the main content portion by processing the at least one sentence vector and the entity vector using a trained neural network, wherein:
the trained neural network comprises a bidirectional long short-term (Bi-LSTM) model; and
the trained neural network is trained to categorize the generated sentence vector and the generated entity vector into a corresponding section type, of the plurality of pre-defined section types; and based on respective content of the sections, generate a medical record according to a pre-defined template, wherein the pre-defined template comprises a plurality of fields, each respective field of the plurality of fields comprises a respective name that matches a respective section type of the pre-defined set of sections, a first field of the plurality of fields matches the section type assigned to the first section of the main content portion, and the first field is filled with one or more values of the at least one medical entity identified in the first section.

17. The computer program product of claim 16, wherein the computer-readable program code is further executable to:

receive the doctor-patient conversation in oral form, and, using speech recognition, transform the oral conversation into a written conversation.

18. The computer program product of claim 16, wherein the doctor-patient conversation includes a plurality of question and answer pairs.

19. The computer program product of claim 16, wherein the pre-defined set of sections of the main content of the doctor-patient conversation includes a chief complaint section, a patient information section, and a medical advice section.

20. The computer program product of claim 16, wherein the pre-defined template is one of a hard medical record format or a soft medical record format.

* * * * *